United States Patent [19]

Kagabu et al.

[11] Patent Number: 5,210,218

[45] Date of Patent: May 11, 1993

[54] 2- AND 3-CHLOROPYRROLES AND PROCESS FOR PREPARING THE SAME

[75] Inventors: Shinzo Kagabu; Itsumi Kawai, both of Gifu; Katsuaki Wada, Oyama, all of Japan

[73] Assignee: Nihon Bayer Agrochem K.K., Tokyo, Japan

[21] Appl. No.: 777,879

[22] Filed: Oct. 15, 1991

[51] Int. Cl.$^5$ ............................................. C07D 207/34
[52] U.S. Cl. ...................................... 548/560; 548/563
[58] Field of Search ................................. 548/563, 560

[56] References Cited

U.S. PATENT DOCUMENTS

| | | | |
|---|---|---|---|
| 3,634,450 | 1/1972 | Last et al. ............................. | 548/563 |
| 4,652,582 | 3/1987 | Wilkerson ....................... | 548/560 X |
| 4,950,678 | 8/1990 | Carney et al. ................... | 548/225 X |
| 5,116,998 | 5/1992 | Lowen ............................... | 548/560 |

OTHER PUBLICATIONS

Chemical Communications, Royal Society of Chemistry, Issue 20, (1990), pp. 1393-1394; Kagabu et al.

*Primary Examiner*—Joseph Paul Brust
*Attorney, Agent, or Firm*—Sprung Horn Kramer & Woods

[57] ABSTRACT

Novel 2- or 3-chloropyrroles represented by the general formula:

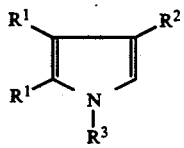

wherein $R^1$ represents hydrogen atom, chlorine atom, alkyl group, or aryl group which may optionally be substituted, with the proviso that any one of the two groups represented by $R^1$ is chlorine atom, $R^2$ represents alkyl group or aryl group which may optionally be substituted, and $R^3$ represents tertiary alkyl group which may be substituted by phenyl, or phenyl which may optionally be substituted, and processes for preparing the same.

2 Claims, No Drawings

2- AND 3-CHLOROPYRROLES AND PROCESS FOR PREPARING THE SAME

The present invention relates to novel 2- or 3-chloropyrroles, and processes for preparing the same.

It is known that N-alkyl- or N-aryl-dihydropyrroles can be prepared by subjecting cyclopropylimines to a pyrolysis operation with the aid of an acid catalyst. It is also known such pyrolysis reactions can be widely utilized for the synthesis of alkaloid compounds (see, for instance, Tetrahedron Lett., 1987, Vol. 28, p. 6597; The Chemistry of the Cyclopropyl Group, 1987, p. 375; ibid, p. 809; and Chem. Rev., 1989, Vol. 89, p. 165).

We have made various studies about the thermal behaviors of halogen-substituted cyclopropylimines, and have now found novel, useful compounds and processes for preparing the same.

Means for Solving the Problem:

The present invention provides novel 2- or 3-chloropyrroles represented by the general formula:

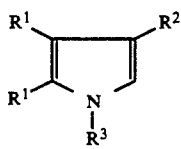 (I)

wherein $R^1$ represents hydrogen atom, chlorine atom, alkyl group, or aryl group which may optionally be substituted, with the proviso that any one of the two groups represented by $R^1$ is chlorine atom,
$R^2$ represents alkyl group or aryl group which may optionally be substituted, and
$R^3$ represents tertiary alkyl group which may be substituted by phenyl, or phenyl which may optionally be substituted.

The compounds of the general formula (I) according to the invention can be prepared by the manufacturing processes shown below.

Process (a):

A process for the production of 3-chloropyrroles represented by the general formula:

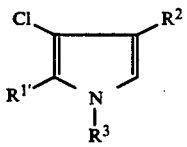 (Ia)

wherein $R^{1'}$ represents hydrogen atom, alkyl group, or optionally substituted aryl group, and
$R^2$ and $R^3$ have the meanings stated above,
characterized in that 2,2-dichlorocyclopropylimines represented by the general formula:

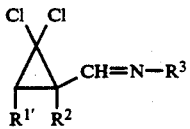 (II)

wherein $R^{1'}$, $R^2$ and $R^3$ have the meanings stated above, are subjected to a heat transition operation in the presence of a polar solvent.

Process (b):

A process for the production of 2-chloropyrroles represented by the general formula:

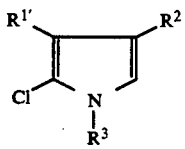 (Ib)

wherein $R^{1'}$, $R^2$ and $R^3$ have the meanings stated above, characterized in that 2,2-dichlorocyclopropylimines represented by the general formula (II) are subjected to a heat transition operation in the presence of an inert solvent and a base.

It is expected that 2- or 3-chloropyrroles of the general formula (I) according to the invention will be useful as novel intermediates in the production of medicines, agricultural chemicals, colorants, photosensitive materials and the like.

In the compounds of the formula (I), according to the invention, alkyl group represented preferably $C_{1-6}$ alkyl, particularly $C_{1-4}$ alkyl, the substituent in aryl and phenyl which may optionally be substituted represents the same or different one to five selected from alkyl, alkoxy, alkylthio and halogen, specifically methyl, ethyl, methoxy, methylthio and chlorine, aryl represents phenyl or naphthyl, and tertially alkyl represents preferably tert-butyl.

The 2,2-dichlorocyclopropylimines of the general formula (II), which are the starting materials in the production of the aimed compounds of the general formula (I), can be obtained according to a known method disclosed in J. Org. Chem. Vol. 54, p. 4275 (1989), by reacting 2,2-dichlorocyclopropanecarbaldehydes represented by the general formula:

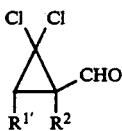 (III)

wherein $R^{1'}$ and $R^2$ have the meanings stated above, with a compound of the general formula:

$H_2N—R^3$ (IV)

wherein $R^3$ has the meaning stated above.

The 2,2-dichlorocyclopropanecarbaldehydes of the general formula (III) can be prepared by subjecting 2,2-dichlorocyclopropanecarbaldehyde diethyl acetals of the general formula:

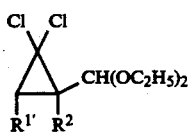 (V)

wherein $R^{1'}$ and $R^2$ have the meanings stated above, to a hydrolysis operation.

The 2,2-dichlorocyclopropanecarbaldehyde diethyl acetals of the general formula (V) can be obtained by a process, wherein acrylaldehyde diethyl acetals of the general formula:

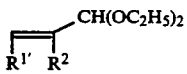 (VI)

wherein $R^{1'}$ and $R^2$ have the meaning stated above,
are subjected together with chloroform to an alkali treatment in the presence of a phase transfer catalyst.

The acrylaldehyde diethylacetals of the general formula (VI) can be obtained according to a method disclosed in Org. Synth. Vol. 60, p. 7 (1981).

The 2,2-dichlorocyclopropanecarbaldehydes of the general formula (III) may also be produced by a method, wherein 2,2-dichlorocyclopropane carbonitriles represented by the general formula:

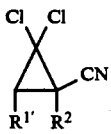 (VII)

wherein $R^{1'}$ and $R^2$ have the meanings stated above, are reduced by employing a diisobutylaluminium hydride.

The 2,2-dichlorocyclopropanecarbonitriles of the general formula (VII) can be obtained by a process, wherein acrylonitriles represented by the general formula:

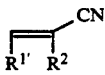 (VIII)

wherein $R^{1'}$ and $R^2$ have the meanings stated above, are subjected to an alkali treatment in the presence of chloroform and also in the presence of a phase transfer catalyst.

As explained above, the compounds of the general formula (Ia) can be produced with high yield and also with high selectivity, by the process (a) according to the invention, wherein the compounds of the general formula (II) are subjected to a thermal transition operation in the presence of a polar solvent.

The compounds of the general formula (Ib) can be prepared with high yield and also with high selectivity, by the process (b) according to the invention, wherein the compounds of the formula (II) are subjected to a thermal transition operation in the presence of an inert solvent and a base.

In carrying out the process (a), it is possible to use any polar solvents as the suitable diluents. Examples of the polar solvents are nitriles such as acetonitrile, benzonitriles, etc.; amides such as dimethylacetamide, dimethylformamide, N-methylpyrrolidone and the like; solfones and sulfoxides such as sulfolane, dimethyl sulfoxide, etc.; esters such as ethyl acetate and the like; and pyridine, 1,1,3,3-tetramethylurea, 1,3-dimethyl-3,4,5,6-tetrahydro-2(1H)pyrimidinone and the like.

In carrying out the process (a), the reaction temperature may be varied within a substantially wide range. In general, the process (a) can be conducted at a temperature of about 100° to 300° C. The reaction may be carried out under a pressure of from normal pressure to 100 atms.

In carrying out the process (b), it is possible to use any inert solvents as the suitable diluents. Such solvents include not only the solvents shown in the descriptions of the process (a), but also non-polar solvents such as anisol, benzene, carbon tetrachloride, chloroform, diethyleneglycol dimethyl ether, diethyleneglycol diethyl ether, tetrahydrofuran, phenetole, cyclohexane, 1,2-dimethoxyethane, dioxane, octane, toluene, xylene, etc.

Suitable bases, employed in carrying out the process (b), include secondary and tertiary alkylamines (with the proviso that each alkyl group has 1 to 10 carbon atoms, and the other proviso that the alkyl groups may form a ring), pyridine, alkyl-substituted pyridine, quinoline, alkyl-substituted quinoline, calcium oxide, magnesium oxide, titanium oxide, zirconium oxide, vanadium oxide, lead oxide, chromium oxide, molybdenum oxide, manganese oxide, iron oxide, cobalt oxide, nickel oxide, platinum oxide, copper oxide, zinc oxide, aluminum oxide, silicon oxide, tin oxide, samarium oxide, barium oxide, potassium carbonate, calcium carbonate, magnesium carbonate, sodium acetate, potassium acetate, sodium hydrogen carbonate, potassium hydrogen carbonate, sodium hydroxide, potassium hydroxide, calcium hydroxide, metal alkoxides (wherein the metal is sodium, magnesium, potassium, lithium, calcium, aluminum or titanium; and the alcohol moiety is a primary, secondary or tertiary alcohol with 1 to 8 carbon atoms).

The process (b) may be conducted under the same temperature and pressure conditions as those employed in the process (a).

Next, the present invention will be further illustrated by way of Examples. However, it should be noted that the scope of the invention is not limited only to these Examples.

EXAMPLES

Preparation of the intermediate compounds represented by the general formula (II)

EXAMPLE 1

2.0 g (0.0093 mol) of 2,2-dichloro-1-phenylcyclopropanecarbaldehyde were dissolved in 16 ml of dry benzene. The resulting benzene solution was admixed with 1.0 g of anhydrous sodium sulfate, and stirred. To the benzene solution was dropwise added a solution of 3.0 g (0.032 mol) of aniline in 4 ml of the same solvent over 15 minutes. After stirring for 86 hours, the reaction mixture was filtered to remove the inorganic substances therefrom. Then the benzene and the aniline were distilled off under a reduced pressure to obtain 1.9 g of 2,2-dichloro-1-phenylcyclopropanemethylidenephenylamine as an oily substance with light yellow color. Yield: 70%.

NS (70eV; relative intensity, %): 289 (M+, 30); 254 (98); 219 (59); 77 (100); 51 (75).

IR ($v cm^{-1}$, film): 1660; 1600; 1500; 760; 700.

EXAMPLE 2

1.1 g (0.0048 mol) of 2,2-dichloro-3-methyl-1-phenylcyclopropanecarbaldehyde were dissolved in 16 ml of dry benzene. The resulting benzene solution was admixed with 0.5 g of anhydrous sodium sulfate, and stirred. To the benzene solution was dropwise added a solution of 1.5 g (0.01 mol) of α,α-dimethylbenzylamine in 4 ml of the same solvent over 15 minutes. After further stirring for 24 hours, the reaction mixture was filtered to remove the inorganic substances therefrom. Then the benzene and the α,α-dimethylbenzylamine were distilled off under a reduced pressure to obtain 1.5 g of 2,2-dichloro-3-methyl-1-phenylcyclopropanemethylidene-α,α-methylbenzylamine as an oily substance with light yellow color. Yield: 88%.

NS (70eV; relative intensity, %): 364 (M+, 12); 192 (42); 119 (100); 177 (46); 91 (62).

IR ($\nu$cm$^{-1}$, film): 1660; 1600; 1490; 1460; 1375; 760; 700.

EXAMPLE 3

1.3 g (0.0057 mol) of 2,2-dichloro-1-methyl-3-phenylcyclopropane carbaldehyde were dissolved in 16 ml of anhydrous benzene. The resulting benzene solution was admixed with 0.5 g of anhydrous sodium sulfate, and stirred. To the benzene solution was dropwise added a solution of 2.0 g (0.027 mol) of t-butylamine in 4 ml of the same solvent over 15 minutes. After further stirring for 94 hours, the reaction mixture was filtered to remove the inorganic substances therefrom. Then the benzene and the t-butylamine were distilled off under a reduced pressure to obtain 1.3 g of 2,2-dichloro-1-methyl-3-phenylcyclopropane-methylidene-t-butylamine as an oily substance with light yellow color. Yield: 81%.

NS (70eV; relative intensity, %): 283 (M+, 1.4); 192 (43); 157 (29); 57 (100); 41 (53).

IR ($\nu$cm$^{-1}$, film): 2960; 1660; 1600; 1460; 1375; 760; 700.

Preparation of the intermediate compounds represented by the general formula (III)

EXAMPLE 4

10.0 g (0.03 mol) of 2,2-dichloro-1-methyl-3-phenylcyclopropanecarbaldehyde diethylacetal were dissolved in a mixed solvent consisting of 18 ml of tetrahydrofuran and 18 ml of water. The resultant solution was admixed with 1 ml of concentrated hydrochloric acid, heated to 60° C. for 5 hours, then cooled, and thereafter admixed with 30 ml of saturated aqueous sodium chloride solution. The organic phase was separated, and the aqueous phase was extracted with isopropyl ether. The organic phase portions were combined together, and dried over anhydrous sodium sulfate. The inorganic substances were removed by filtration. The organic solvent was distilled off under a reduced pressure, and the remaining oily substance was subjected to a distillation operation under a pressure of 0.1 mmHg. At a temperature of 115°-117° C., there was obtained a fraction containing 2,2-dichloro-1-methyl-3-phenylcyclopropanecarbaldehyde. Yield: 5.5 g (80.4%).

Melting point: 50°-50.5° C.

EXAMPLE 5

7.5 g (0.033 mol) of 2,2-dichloro-3-methyl-1-phenylcyclopropane carbonitrile were dissolved in 70 ml of dry benzene, and cooled with ice. To the resulting solution were dropwise added 25 ml of a 25% solution of diisobutylaluminium hydride in toluene in nitrogen atmosphere. The reaction mixture was stirred in nitrogen atmosphere at room temperature for 24 hours, and then further stirred at 35° C. for 5 hours. The reaction solution was cooled with ice, and admixed with 20 ml of methanol to decompose the excess diisobutylaluminium hydride. Thereafter, the reaction solution was poured into 150 ml of saturated aqueous ammonium chloride solution, and stirred for 20 minutes. 40 ml of a 10% dilute sulfuric acid were added to the reaction mixture to separate the organic phase. The aqueous phase was extracted with ether. The combined organic phase was washed with a saturated aqueous sodium hydrogen carbonate solution and then with a saturated aqueous sodium chloride solution, and dried over anhydrous sodium sulfate. The inorganic substances were filtered off, and the organic solvent was distilled off under a reduced pressure. The resultant oily residue was subjected to a distillation operation under a pressure of 0.1 mmHg (118°-119° C.) to obtain 4.5 g of 2,2-dichloro-3-methyl-1-phenylcyclopropanecarbaldehyde. Yield: 60%.

Preparation of the intermediate compounds represented by the general formula (V)

EXAMPLE 6

A three-neck flask was charged with 20.4 g (0.09 mol) of α-methyl-β-phenylacrylaldehyde diethyl acetal, 22.1 g of chloroform, 0.2 g of triethylbenzylammonium chloride and 10.2 g of methylene chloride, and the resulting solution was stirred. To this solution were dropwise added 36 ml of a 50% sodium hydroxide solution at a temperature of 40° C. The reaction solution was heated under reflux at the same temperature for 10 hours. The reaction solution was poured into ice water, and the organic phase was separated. The aqueous phase was extracted with isopropyl ether. The combined organic phase was dried over anhydrous sodium sulfate. The inorganic substances were filtered off, and the organic solvent was distilled off under a reduced pressure. The resultant oily residue was subjected to a distillation operation under a pressure of 0.1 mmHg. At a temperature of 135°-145° C., there was obtained a fraction containing 2,2-dichloro-1-methyl-3-phenylcyclopropanecarbaldehyde diethylacetal. Yield: 10.2 g (36.6%).

Preparation of the intermediate compounds represented by the general formula (VII)

EXAMPLE 7

A three-neck flask was charged with a mixture of 20 g (0.14 mol) of 2-phenyl-2-butenonitrile, 200 g of chloroform and 2 g of triethylbenzylammonium chloride, and the mixture was stirred. To the mixture were dropwise added 100 g of a 50% sodium hydroxide solution under cooling with ice. The reaction mixture was further stirred at room temperature for 15 hours, then poured into ice water, and the organic phase was separated. The aqueous phase was extracted with hexane. The organic phase fractions were combined together, and dried over anhydrous sodium sulfate. The inorganic substances were filtered off, and the organic solvent was distilled off under a reduced pressure. The resultant oily residue was distilled under a pressure of 0.1 mmHg (116°-120° C.) to obtain 10.4 g of 2,2-dichloro-3-methyl-1-phenylcyclopropanecarbonitrile. Yield: 33%.

Preparation of the compounds represented by the general formula (I)

EXAMPLE 8

A 200 ml stainless steel pressure reaction vessel was charged with a solution of 974 mg (3.62 mmol) of 2,2-dichloro-1-phenylcyclopropanemethylidene-t-butylamine in 100 ml of dry N-methylpyrrolidone. A nitrogen gas was passed to the reactor for 5 minutes, and then the reactor was sealed and heated to 210° C. for 22 hours. After cooling to room temperature, a substantial portion of the solvent was removed from the reaction solution under a relatively low pressure (up to 100 mmHg) by means of a Vigrex distilling tube. The residue was dissolved in benzene, and washed with a 1% hydrochloric acid, then with a 5% aqueous sodium carbonate solution and finally with a saturated aqueous sodium chloride solution. Then the reaction mixture was dried over anhydrous sodium sulfate, the inorganic substances were filtered off, and the organic solvent was distilled off under reduced pressure. The resulting residue was treated in a silica gel column by using hexane/isopropyl ether (10:1) as the eluant. 633 mg of 1-t-butyl-3-chloro-4-phenylpyrrole were obtained as an oily substance with light yellow color. Yield: 75%.

PMR (CDCl$_3$; TMS; δ=ppm): 7.6 (m, 2H); 7.2-7.5 (m, 3H); 6.89 (d, 1H, J=2.93 Hz); 6.83 (d, 1H, J=2.93 Hz); 1.53 (s, 9H).

MLMS: obs.: 233.0973 (calc.: 233.00968).

In a manner similar to the above, the following compounds were prepared.

1-cumyl-3-chloro-4-phenylpyrrole
Yield: 90%
MLMS: obs.: 295.1143 (calc.: 295.1128).
PMR (CDCl$_3$; TMS; δ=ppm): 7.6 (m, 2H); 7.19-7.36 (m, 6H); -7.08 (m, 2H); 6.84 (d, 1H, J=2.75 Hz); 6.76 (d, 1H, J=2.74 Hz); 1.85 (s, 6H).

1-cumyl-3-chloro-4-methylpyrrole
Yield: 72%
MLMS: obs.: 233.0988 (calc.: 233.0968).
PMR (CDCl$_3$; TMS; δ=ppm): 7.0-7.3 (m, 5H); 6.66 (d, 1H, J=2.93 Hz); 6.32 (d, 1H, J=2.93 Hz); 2.03 (s, 3H); 1.82 (s, 6H).

3-chloro-1,4-diphenylpyrrole
Yield: 81%
Melting point: 82° C.
PMR (CDCl$_3$; TMS; δ=ppm): 7.63 (m, 2H); 7.23-7.5 (m, 8H); 7.15 (d, 1H, J=2.6 Hz); 7.12 (d, 1H, J=2.6 Hz).

1-cumyl-3-chloro-4-methyl-2-phenylpyrrole
Yield: 78%
Melting point: 142° C.
PMR (CDCl$_3$; TMS; δ=ppm): 7.23 (m, 2H); 6.9-7.2 (m, 6H); 6.86 (s, 1H); 6.63 (m, 2H); 2.14 (s, 3H); 1.66 (s, 6H).

1-t-butyl-3-chloro-4-methyl-2-phenylpyrrole
Yield: 73%
MLMS: obs.: 247.1136 (calc.: 247.1124).
PMR (CDCl$_3$; TMS; δ=ppm): 7.2-7.4 (m, 5H); 6.66 (s, 1H); 1.37 (m, 9H).

EXAMPLE 9

1.9 g (0.7 mmol) of 2,2-dichloro-3-methyl-1-phenylcyclopropanemethylidene-α,α-dimethylbenzylamine were dissolved in 30 ml of dry phenetol. To the resulting solution were added 1.9 g of dry calcium oxide. The reaction mixture was heated to 170° C. under reflux for 24 hours, then the calcium oxide was filtered off, and the phenetol was removed from the reaction mixture by distillation under a pressure of 20 mmHg by employing a Vigrex distilling tube. The resulting residue was extracted with isopropyl ether, and washed with a 1% hydrochloric acid, then with a 5% aqueous sodium carbonate solution and finally with a saturated aqueous sodium chloride solution. After the reaction mixture had been dried, the solvent was removed, and the remaining crystalline substance was recrystallized from hexane to obtain 1.28 g of 1-cymyl-2-chloro-3-methyl-4-phenylpyrrole.

Yield: 76%; melting point: 103° C.

Elementary analysis: obs.: C: 77.01; H: 6.05; N: 4.90%; calc.: C: 77.15; H: 6.13; N: 4.74%.

PMR (CDCl$_3$; TMS; δ=ppm): 7.51 (m, 2H); 7.15-7.4 (m, 6H); 7.1 (m, 2H); 7.28 (d, 1H, J=2.6 Hz); 6.41 (d, 1H, J=2.6 Hz); 1.98 (s, 6H).

EXAMPLE 10

50 mg (0.15 mmol) of 2,2-dichloro-3-methyl-1-phenylcyclopropanemethylidene-α,α-dimethylbenzylamine were dissolved in 25 ml of dry phenetol. To the resulting solution were added 89 mg of dry calcium oxide. The reaction mixture was heated to 170° C. under reflux for 17 hours, then the inorganic compound was filtered off, and the phenetol was removed from the reaction mixture by distillation under a pressure of 20 mmHg by employing a Vigrex distilling tube. The resulting residue was extracted with isopropyl ether, and washed with a 1% hydrochloric acid, then with a 5% aqueous sodium carbonate solution and finally with a saturated aqueous sodium chloride solution. After the reaction mixture had been dried, the solvent was distilled off, and the remaining crystalline substance was recrystallized from hexane to obtain 33 mg of the same compound as that shown in Example 9. Yield: 71%.

EXAMPLE 11

664 mg (2.0 mmol) of 2,2-dichloro-3-methyl-1-phenylcyclopropanemethylidene-α,α-dimethylbenzylamine were dissolved in 50 ml of dry phenetol. To the resulting solution were added 1.212 mg of dry diisopropylamine. The reaction mixture was heated to 170° C. under reflux for 14 hours, then the inorganic compound was filtered off, and the phenetol was removed from the reaction mixture by distillation under a pressure of 20 mmHg by employing a Vigrex distilling tube. The resultant residue was extracted with isopropyl ether, and washed with a 1% hydrochloric acid, then with a 5% aqueous sodium carbonate solution and finally with a saturated aqueous sodium chloride solution. After the reaction mixture had been dried, the solvent was removed, and the remaining crystalline substance was recrystallized from hexane to obtain 516 mg of the same compound as that shown in Example 9. Yield: 87.5%.

EXAMPLE 12

1.60 g (4.8 mmol) of 2,2-dichloro-1-phenylcyclopropanemethylidene-phenylamine were dissolved in 50 ml of dry phenetol. To the resulting solution were added 1.70 g of dry calcium oxide. The reaction mixture was heated to 170° C. under reflux for 21 hours, then the inorganic compound was filtered off, and the phenetol was removed from the reaction mixture by distillation under a pressure of 20 mmHg by employing a Vigrex distilling tube. The resulting residue was extracted with isopropyl ether, and washed with a 1% hydrochloric acid, then with a 5% aqueous sodium carbonate solution and finally with a saturated aqueous sodium chloride solution. After the reaction mixture had been dried, the solvent was distilled off to obtain, as a residue, 1.19 g of 2-chloro-1,4-diphenylpyrrole having a purity of at most 85%. This compound is apt to decompose, and therefore a sample of the compound for analysis was isolated by means of a gas chromatography for separation (OV1, 1%, column temperature: 10° C.).

MLMS: obs.: 253.0658 calc.: 253.0656 (as C$_{16}$H$_{12}$ClN)

PMR (CDCl$_3$; TMS; δ=ppm): 7.1-7.6 (m, 10H); 7.40 (d, 1H, J=2.2 Hz); 6.68 (d, 1H, J=2.2 Hz).

We claim:

1. A 2- or 3-chloropyrrole of the formula

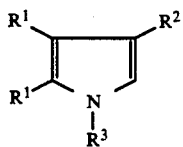

in which

R[1] is chlorine and the other one

R[1] is hydrogen, $C_{1-6}$-alkyl, or phenyl or naphthyl optionally substituted by at least one member selected from the group consisting of $C_{1-6}$-alkyl, $C_{1-6}$-alkoxy, $C_{1-6}$-alkylthio and halogen, R[2] is phenyl or naphthyl optionally substituted by at least one member selected from the group consisting of $C_{1-6}$-alkyl, $C_{1-6}$-alkoxy, $C_{1-6}$-alkylthio and halogen, and R[3] is tertiary alkyl of up to 6 carbon atoms optionally substituted by phenyl or is phenyl.

2. A compound according to claim 1, wherein such compound is 1-t-butyl-3-chloro-4-phenylpyrrole of the formula

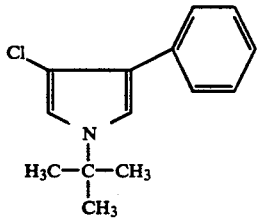

* * * * *